United States Patent [19]

Glackin et al.

[11] Patent Number: 5,618,280
[45] Date of Patent: Apr. 8, 1997

[54] DIAPER

[75] Inventors: George B. Glackin, Wyoming; Cynthia J. Panning, Cincinnati, both of Ohio; Laura G. Van Rijswijck, Burlington, Ky.

[73] Assignee: The Procter & Gamble Company, Cincinnati, Ohio

[21] Appl. No.: 491,559

[22] Filed: Jun. 16, 1995

[51] Int. Cl.⁶ .............................. A61F 13/15; A61F 13/20
[52] U.S. Cl. ...................... 604/385.1; 604/391; 604/386
[58] Field of Search .................................. 604/361, 365, 604/367, 374, 375, 377, 378, 385.1, 385.2

[56] References Cited

U.S. PATENT DOCUMENTS

| | | | |
|---|---|---|---|
| 3,779,246 | 12/1973 | Mesek et al. | 128/287 |
| 3,949,130 | 4/1976 | Sabee et al. | 604/365 |
| 4,205,679 | 6/1980 | Repke et al. | 128/287 |
| 4,475,912 | 10/1984 | Coates | 604/385.1 |
| 4,646,362 | 3/1987 | Heran et al. | 2/400 |
| 4,753,649 | 6/1988 | Pazdernik | 604/389 |
| 4,861,652 | 8/1989 | Lippert et al. | 604/383 |
| 4,963,140 | 10/1990 | Robertson et al. | 604/389 |
| 5,176,670 | 1/1993 | Roessler et al. | 604/391 |
| 5,288,546 | 2/1994 | Roessler et al. | 604/385.1 |
| 5,399,174 | 3/1995 | Yeo et al. | 604/365 |
| 5,522,809 | 6/1996 | Larsonneur | 604/361 |

*Primary Examiner*—Robert A. Clarke
*Assistant Examiner*—Ki Yong O
*Attorney, Agent, or Firm*—Kevin C. Johnson; Steven W. Miller; Jacobus C. Rasser

[57] ABSTRACT

An absorbent article such as a disposable diaper, incontinence brief, diaper holder, training pant and the like, having an improved backsheet providing moisture imperviousness and also providing a textile feel and look for the absorbent article. Such absorbent articles have a rear waist region, a front waist region, a crotch region, a central region, a pair of side regions, a pair of longitudinal edges, and a pair of end edges. The absorbent articles include a liquid impervious topsheet, a backsheet joined to the topsheet and an absorbent core positioned between the topsheet and the backsheet. The backsheet includes an inner layer of liquid impervious plastic material and an outer layer of nonwoven fibrous material wherein the outer layer is positioned between the side regions and extends from the rear waist region to the front waist region of the diaper.

6 Claims, 4 Drawing Sheets

DIAPER

FIELD OF INVENTION

The present invention relates to absorbent articles such as diapers, incontinence briefs, diaper holders, training pants and the like, and more particularly, to absorbent articles having an improved backsheet.

BACKGROUND OF THE INVENTION

Infants and other incontinent individuals wear absorbent articles such as diapers to receive and contain urine and other body exudates. Absorbent articles function both to contain discharged materials and to isolate the materials from the body of the wearer and from the wearer's garments and bed clothing. Disposable absorbent articles having many different basic designs are known to the art.

A common form of a disposable absorbent article comprises a liquid pervious topsheet, an absorbent core and a liquid impervious backsheet, such as a polyethylene film. One of the obstacles that manufacturers of such disposable absorbent articles must overcome is that a certain number of mothers object to the feel of the diaper, and particularly object to the feel of the polyethylene film. Even though disposable diapers such as those disclosed in U.S. Pat. No. 3,860,003 entitled "Contractible Side Portions for Disposable Diaper" issued to Buell on Jan. 14, 1975, minimize and effectively eliminate contact between the backsheet and the infant's skin, many mothers remain convinced that plastic materials are not comfortable to an infant, and hence are reluctant to even try, let alone use, disposable diapers that include an exposed plastic backsheet. To meet this concern, disposable diaper manufacturers have devoted substantial time and effort to improve the feel and appearance of their products.

One solution to the above problem that has been proposed is to completely eliminate the plastic backsheet and replace it with a woven or nonwoven fabric that has been treated to be water-repellent. However, it has been found that it has not been possible to make a fibrous web sufficiently water-repellent to hold a large quantity of liquid within the diaper without sacrificing the sought after soft feel.

Another solution to the above problem that has been proposed is to deeply emboss the polyethylene backsheet to improve its drape and feel. A diaper with a deeply embossed backsheet has substantially improved drape and feel characteristics over a diaper wherein the backsheet is not embossed, or even lightly embossed, but such a backsheet still has the feel of a polyethylene film.

Another solution to the above problem that has been proposed is to adhere a fibrous outer layer to the plastic inner layer. A diaper with a fibrous outer layer adhered to the plastic inner layer not only has a pleasant external feel, but also enables a thinner gauge, less costly material to be used for the plastic layer, thereby making the diaper less stiff and more conformable. However, it has been found that adhering a nonwoven outer layer to the plastic inner layer adds some complexity in the manufacturing process such as the ability to secure fastening tapes to the disposable diaper. In addition, it has been found that the nonwoven when added to the plastic layer tends to inhibit the extensibility of the portions of the diaper which are intended to be extensible, e.g., the elasticized side panels.

Thus, it is an object of the present invention to provide a disposable absorbent article with a fibrous outer layer that simplifies the manufacturing process and does not inhibit the extensibility of the extensible portions of the diaper.

It is a further object of the present invention to provide a disposable absorbent article having a fibrous outer layer providing improved feel and comfort for the wearer.

These and other objectives of the present invention will be more readily apparent when considered in reference to the following description and when taken in conjunction with the accompanying drawings.

SUMMARY OF THE INVENTION

The present invention provides absorbent articles such as disposable diapers, incontinence briefs, diaper holders, training pants and the like, having an improved backsheet providing moisture imperviousness and also providing a textile feel and look for the absorbent article. Such absorbent articles comprise a rear waist region, a front waist region, a crotch region, a central region, a pair of side regions, a pair of longitudinal edges, and a pair of end edges. The absorbent articles further comprise a liquid impervious topsheet, a backsheet joined to the topsheet and an absorbent core positioned between the topsheet and the backsheet. The backsheet includes an inner layer of liquid impervious plastic material and an outer layer of nonwoven fibrous material wherein the outer layer is positioned between the side regions and does not extend into the side regions. The outer layer extends from the rear waist region to the front waist region of the diaper, and preferably,. forms a portion of each of the end edges.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinence briefs, incontinence undergarments, diaper holders and liners, feminine hygiene garments, training pants, and the like.

Figure 1:
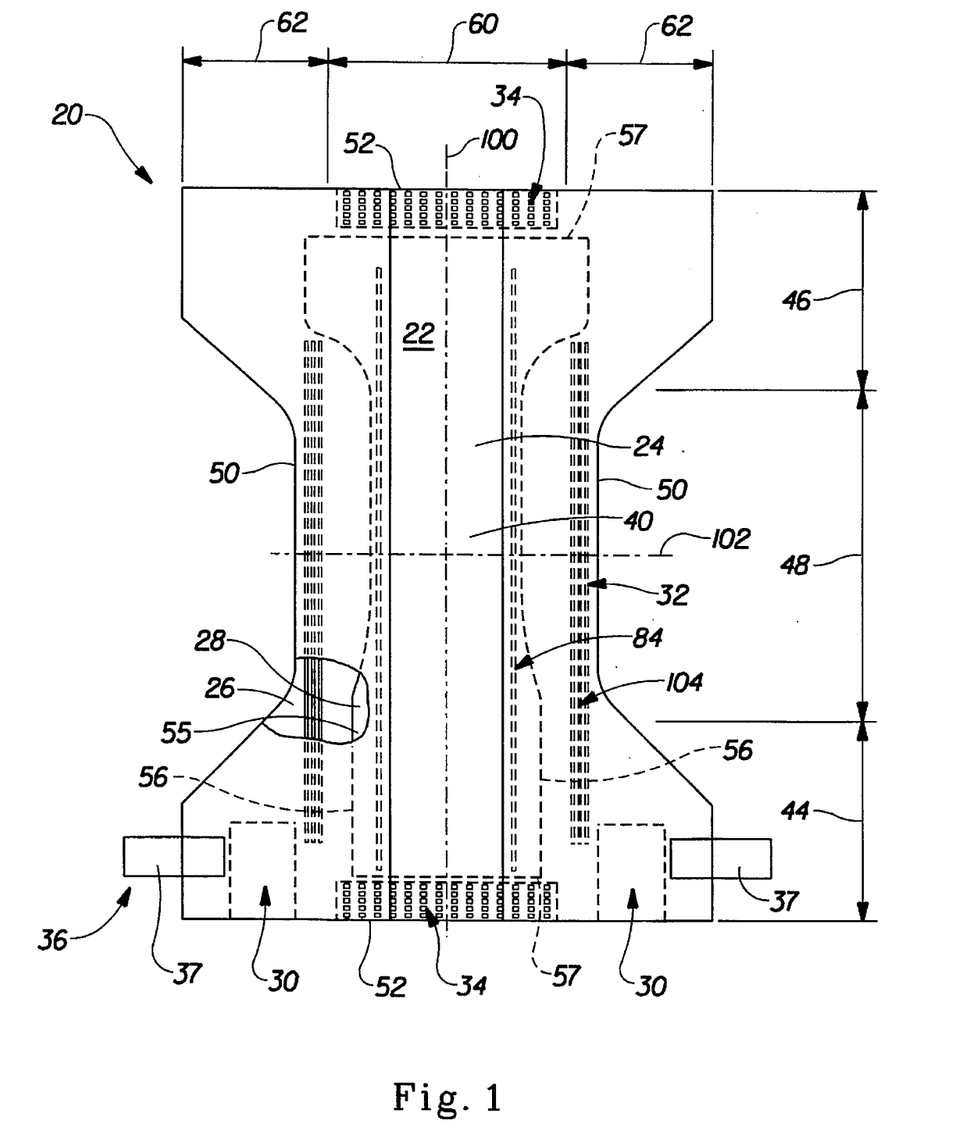
FIG. 1 is a plan view of a disposable diaper embodiment of the present invention having portions cut away to reveal underlying structure, the inner surface of the diaper is facing the viewer.

FIG. 1 is a plan view of the diaper 20 of the present invention in its flat-out, uncontracted state (i.e., with elastic induced contraction pulled out) with portions of the structure being cut-away to more clearly show the construction of the diaper 20 and with the portion of the diaper 20 which faces the wearer, the inner surface 40, facing the viewer. As shown in FIG. 1, the diaper 20 preferably comprises a containment assembly 22 comprising a liquid pervious topsheet 24; a liquid impervious backsheet 26 joined to the topsheet; and an absorbent core 28 positioned between the topsheet 24 and the backsheet 26. The diaper preferably further comprises elasticized side panels 30; elasticized leg cuffs 32; elasticized waistbands 34; and a fastening system 36 preferably comprising a pair of securement members 37 and a landing member 38, (shown in FIG. 2).

The diaper 20 is shown in FIG. 1 to have an inner surface 40 (facing the viewer in FIG. 1 ), an outer surface 42 opposed to the inner surface 40, a rear waist region 44, a front waist region 46 opposed to the rear waist region 44, a crotch region 48 positioned between the rear waist region 44 and the front waist region 46, and a periphery which is defined by the outer perimeter or edges of the diaper 20 in which the longitudinal edges are designated 50 and the end edges are designated 52. The inner surface 40 of the diaper 20 comprises that portion of the diaper 20 which is positioned adjacent to the wearer's body during use (i.e., the inner surface 40 generally is formed by at least a portion of the topsheet 24 and other components joined to the topsheet 24). The outer surface 42 comprises that portion of the diaper 20 which is positioned away from the wearer's body (i.e., the outer surface 42 is generally formed by at least a portion of the backsheet 26 and other components joined to the backsheet 26). As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. The rear waist region 44 and the front waist region 46 extend from the end edges 52 of the periphery to the crotch region 48. The diaper 20 also has a central region 60 and a pair of side regions 62. The central region 60 is positioned between the two side regions 62.

The diaper 20 also has two centerlines, a longitudinal centerline 100 and a transverse centerline 102. The term "longitudinal", as used herein, refers to a line, axis, or direction in the plane of the diaper 20 that is generally aligned with (e.g. approximately parallel with) a vertical plane which bisects a standing wearer into left and right halves when the diaper 20 is worn. The terms "transverse" and "lateral", as used herein, are interchangeable and refer to a line, axis or direction which lies within the plane of the diaper that is generally perpendicular to the longitudinal direction (which divides the wearer into front and back body halves).

The containment assembly 22 of the diaper 20 is shown in FIG. 1 as comprising the main body (chassis) of the diaper 20. The containment assembly 22 comprises at least topsheet 24, backsheet 26 and absorbent core 28. When the absorbent article comprises a separate holder and a liner, the containment assembly 22 generally comprises the holder and the liner (i.e., the containment assembly 22 comprises one or more layers of material to define the holder while the liner comprises an absorbent composite such as a topsheet, a backsheet, and an absorbent core.) For unitary absorbent articles, the containment assembly 22 comprises the main structure of the diaper with other features added to form the composite diaper structure. Thus, the containment assembly 22 for the diaper 20 generally comprises the topsheet 24, the backsheet 26, and the absorbent core 28.

Figure 2:
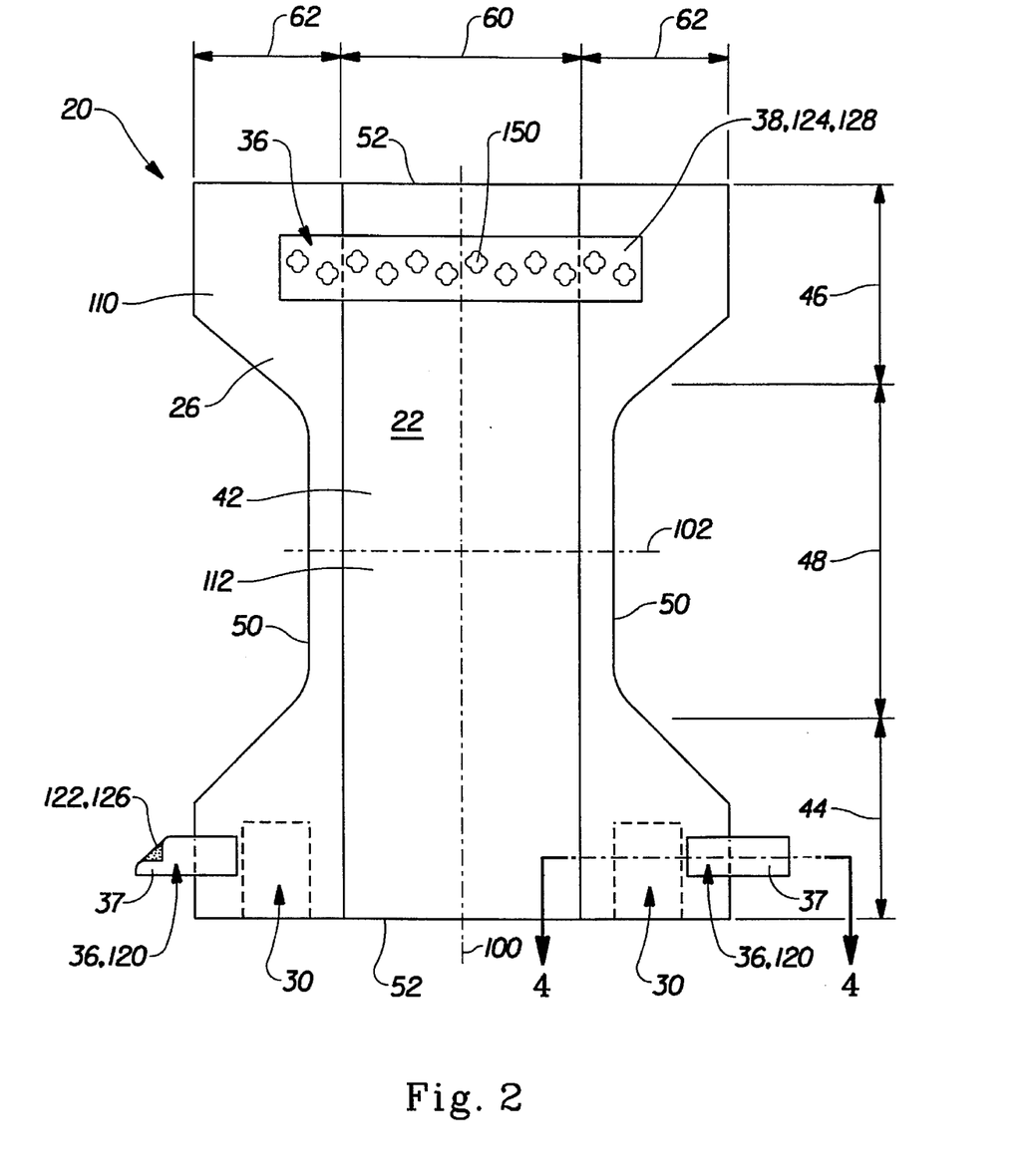
FIG. 2 is a plan view of a disposable diaper embodiment of the present invention, the outer surface of the diaper is facing the viewer.

FIGS. 1 and 2 show a preferred embodiment of the containment assembly 22 in which the topsheet 24 and the backsheet 26 have length and width dimensions generally larger than those of the absorbent core 28. The topsheet 24 and the backsheet 26 extend beyond the edges of the absorbent core 28 to thereby form the periphery of the diaper 20. While the topsheet 24, the backsheet 26, and the absorbent core 28 may be assembled in a variety of well known configurations, exemplary containment assembly configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge" which issued to Kenneth B. Buell et al., on Sep. 29, 1992; each of which is incorporated herein by reference.

The absorbent core 28 may be any absorbent member which is generally compressible, conformable, non-irritating to the wearer's skin, and capable of absorbing and retaining liquids such as urine and other certain body exudates. As shown in FIG. 1, the absorbent core 28 has a garment-facing side 54, a body-facing side 55, a pair of side edges designated 56, and a pair of waist edges designated 57. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 28 may vary (e.g., the absorbent core may have varying caliper zones, a hydrophilic gradient, a superabsorbent gradient, or lower average density and lower average basis weight acquisition zones; or may comprise one or more layers or structures). Further, the size and absorbent capacity of the absorbent core 28 may also be varied to accommodate wearers ranging from infants through adults. However, the total absorbent capacity of the absorbent core 28 should be compatible with the design loading and the intended use of the diaper 20.

One embodiment of the diaper 20 has an asymmetric, modified T-shaped absorbent core 28 having ears in the front waist region but a generally rectangular shape in the rear waist region. Exemplary absorbent structures for use as the absorbent core 28 of the present invention that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The absorbent core may further comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. All of these patents are incorporated herein by reference.

The backsheet 26 of the present invention performs the dual functionality of providing moisture imperviousness and also providing a textile feel and look for the diaper 20. For this purpose, referring now to FIG. 2, the backsheet 26 comprises a two-layer composite material having an inner layer 110 and an outer layer 112.

The inner layer 110 of backsheet 26 is positioned adjacent the garment-facing surface 54 of the absorbent core 28 and is preferably joined thereto by attachment means (not shown) such as those well known in the art. For example, the inner layer 110 may be secured to the absorbent core 28 by a uniform continuous layer of to adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. An example of a suitable attachment means comprising an open pattern network of filaments of adhesive is disclosed in U.S. Pat. No. 4,573,986 entitled "Disposable Waste-Containment Garment", which issued to Minetola et al. on Mar. 4, 1986. Another suitable attachment means comprising several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art. Embodiments of the present invention are also contemplated wherein the absorbent core is not joined to the inner layer 110, the topsheet 24, or both in order to provide greater extensibility in the front waist region 46 and the rear waist region 44.

The inner layer 110 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The inner layer 110 prevents the exudates absorbed and contained in the absorbent core 28 from wetting articles which contact the diaper 20 such as bedsheets and undergarments, however, the inner layer 110 may permit vapors to escape from the absorbent core 28 (i.e., is breathable). Thus, the inner layer 110 preferably comprises a polymeric film such as thermoplastic films of polyethylene or polypropylene. A suitable material for the inner layer 110 is a thermoplastic film having a thickness of from about 0.012 mm (0.5 mil) to about 0.051 mm (2.0 mils).

In preferred embodiments of the present invention, at least a portion of the inner layer 110 is subjected to mechanical stretching in order to provide a "zero strain" stretch laminate that forms the elasticized side panels 30. The inner layer 110 can be prestrained by directing the inner layer through an incremental mechanical stretching system similar to the operation described with respect to the formation of the "zero strain" stretch laminate backsheet and elasticized side panels in U.S. Pat. No. 5,151,092 entitled "Absorbent Article With Dynamic Elastic Waist Feature Having A Predisposed Resilient Flexural Hinge", issued to Buell et al., on Sep. 29, 1992. Accordingly, the inner layer 110 is preferably elongatable, more preferably drawable, but not necessarily elastomeric, so that the inner layer 110 will, upon mechanical stretching, be at least to a degree permanently elongated such that it will not fully return to its original undistorted configuration. In preferred embodiments, the inner layer 110 can be subjected to mechanical stretching without undue rupturing or tearing. Thus, it is preferred that the inner layer 110 have an ultimate elongation to break of at least 400% to about 700% in the cross-machine direction as measured using a method consistent with ASTM (American Society of Testing Materials) D-638. Films suitable for use as the inner layer 110 generally contain a high content of linear low density polyethylene. The Clopay Corporation of Cincinnati, Ohio, manufactures a suitable inner layer under the designation 1401. Other suitable materials for the inner layer include RR8220 blown films and RR5475 east films as manufactured by Tredegar Industries, Inc. of Terre Haute, Ind.

The size of the inner layer 110 is dictated by the size of the absorbent core 28 and the exact diaper design selected. In a preferred embodiment, the inner layer 110 has a modified hourglass shape extending beyond the absorbent core a minimum distance of about 1.3 cm to about 2.5 cm (about 0.5 to about 1.0 inch) around the entire diaper periphery. Preferably, the inner layer 110 is much wider than the absorbent core in the rear waist region 44 so that the side regions 62 in the rear waist region 44 are generally wider in the lateral direction than the side regions 62 in the front waist region 46.

The outer layer 112 most preferably consists of a layer of nonwoven fibrous material. Materials suitable for the outer layer 112 include a spun-bonded nonwoven web of synthetic fibers such as polypropylene, polyethylene, or polyester fibers; a nonwoven web of cellulosic fibers, textile fibers such as rayon fibers, cotton and the like, or a blend of cellulosic and textile fibers; a spun-bonded nonwoven web of synthetic fibers such as polypropylene, polyethylene or polyester fibers mixed with cellulosic, pulp fibers or textile fibers; or melt blown thermoplastic fibers, such as macrofibers or microfibers, of polypropylene, polyethylene, polyester or other thermoplastic materials or mixtures of such thermoplastic macrofibers or microfibers with cellulosic, pulp or textile fibers.

The inner layer 110 and the outer layer 112 of the backsheet 26 are advantageously bonded to one another, by any means appropriate for the specific materials selected for the two layers. The two layers can be laminated using heat or pressure or both heat and pressure. The two layers can also be bonded with adhesive, heat-sealing or ultrasonic sealing. In addition, thermoplastic polymeric material of the inner layer 110 can be extrusion coated onto the nonwoven outer layer 112. If desired, the textile effect of the nonwoven outer layer 112 can be further enhanced by various embossing patterns. Likewise, the inner layer 110 may be embossed to provide it with a textile appearance.

In the embodiment shown in FIG. 2, the outer layer 112 is positioned within the central region 60 and extends from at least the rear waist region 44 to the front waist region 46. Preferably, the outer layer 120 forms a portion of the end edge 52 in the rear waist region 44 and a portion of the end edge 52 in the front waist region 46. The outer layer 112 is positioned between the side regions 66 within the central region 60 and does not extend into the side regions 62. Positioning the outer layer 112 within the central region 60 of the diaper, allows the securement members 37 to be joined directly to the inner layer of liquid impervious plastic material 110. Thus, the securement members 37 are not joined either directly or indirectly to any portion of the outer layer 112. Attaching the securement members 37 directly to the inner layer of liquid impervious plastic material 110 provides a more secure attachment than attaching the securement members 37 to a nonwoven fibrous material. Securement members attached to a nonwoven fibrous material sometimes separate from the diaper when the diaper is applied and/or worn. Attaching the securement members 37 directly to the inner layer of liquid impervious plastic material 110 reduces the likelihood that the securement members 37 will separate from the diaper when the diaper is applied and/or worn. In addition, the nonwoven outer layer 112 does not inhibit the extensibility of the elasticized side panels 30 positioned in the side region 62 in the rear waist region 44 allowing the elasticized side panels 30 to be fully extensible.

Figure 3:
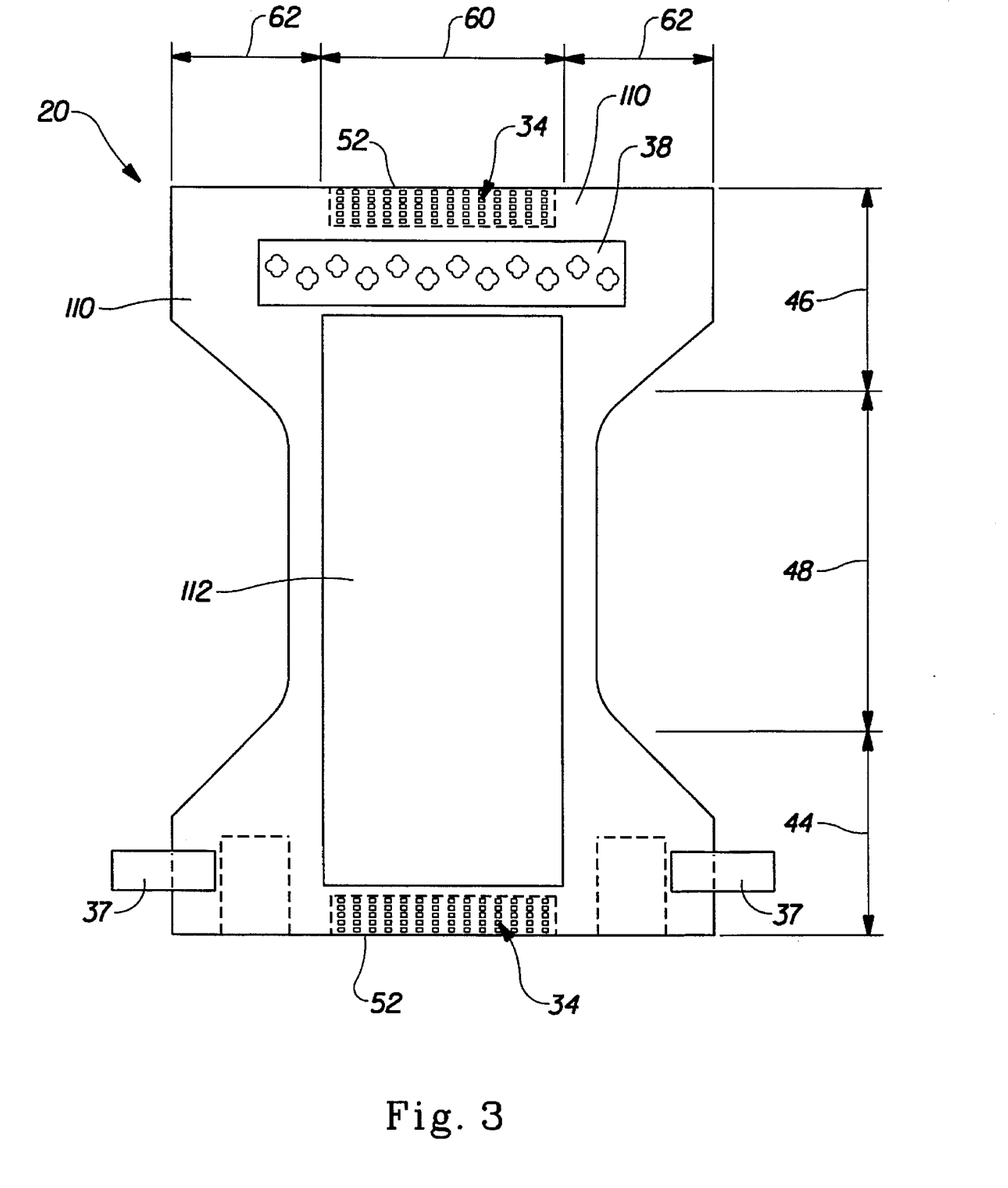
FIG. 3 is a plan view of another disposable diaper embodiment of the present invention, the outer surface of the diaper is facing the viewer.

In another embodiment shown in FIG. 3, the outer layer 112 is positioned within the central region 60 between the side regions 62 and extends longitudinally from the rear waist region 44 to the rear waist region 46. In this embodiment the landing member 38 is secured directly to the inner layer 110 as the outer layer 112 does not extend beyond the landing member 38 in the front waist region 46. Furthermore, the outer layer 112 does not extend over the elasticized waistbands 34.

The topsheet 24 is positioned adjacent the body-facing surface 55 of the absorbent core 28 and is preferably joined thereto and to the inner layer 110 of backsheet 26 by attachment means (not shown) such as those well known in the art. Suitable attachment means are described with respect to joining the inner layer 110 to the absorbent core 28. In a preferred embodiment of the present invention, the topsheet 24 and the inner layer 110 are joined directly to each other in the diaper periphery and are indirectly joined together by directly joining them to the absorbent core 28 by the attachment means (not shown).

The topsheet 24 is compliant, soft feeling, and non-irritating to the wearer's skin. Further, the topsheet 24 is preferably liquid pervious permitting liquids (e.g., urine) to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is preferably made of a hydrophobic material to isolate the wearer's skin from liquids which have passed through the topsheet 24 and are contained in the absorbent core 28 (i.e. to prevent rewet). If the topsheet 24 is made of a hydrophobic material, at least the upper surface of the topsheet 24 is treated to be hydrophilic so that liquids will transfer through the top sheet more rapidly. This diminishes the likelihood that body exudates will flow off the topsheet 24 rather than being drawn through the topsheet 24 and being absorbed by the absorbent core 28. The topsheet 24 can be rendered hydrophilic by treating it with a surfactant. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991, each of which is incorporated by reference herein.

In a preferred embodiment of the present invention, at least a portion of the topsheet 24 is subjected to mechanical stretching in order to provide a "zero strain" stretch laminate that forms the elasticized side panels 30. The topsheet 24 can be prestrained by any methods as are known in the art including, but not limited to, the methods described herein with respect to the formation of the "zero strain" stretch backsheet. Thus, the topsheet 24 is preferably elongatable, more preferably drawable, but not necessarily elastomeric, so that the topsheet 24 will, upon mechanical stretching, be at least to a degree permanently elongated such that it will not fully return to its original configuration. In preferred embodiments, the topsheet 24 can be subjected to mechanical stretching without undue rupture or tearing. Thus, it is preferred that the topsheet 24 have a low cross-machine direction (lateral direction) yield strength.

There are a number of manufacturing techniques which may be used to manufacture the topsheet 24. For example, the topsheet 24 may be a nonwoven web of fibers. When the topsheet 24 comprises a nonwoven web, the web may be spunbonded, carded, wet-laid, melt-blown, hydroentangled, combinations of the above, or the like. A suitable topsheet 24 is carded and thermally bonded by means well known to those skilled in the fabrics art. A satisfactory topsheet 24 comprises staple length polypropylene fibers having a denier of about 2.2 As used herein, the term "staple length fibers" refers to those fibers having a length of at least about 15.9 mm (0.625 inches). Preferably, the topsheet 24 has a basis weight from about 14 to about 25 grams per square meter. A suitable topsheet is manufactured by Veratec, Inc., a Division of International Paper Company, of Walpole, Mass. under the designation P-8.

The diaper 20 preferably further comprises elasticized leg cuffs 32 for providing improved containment of liquids and other body exudates. Each elasticized leg cuff 32 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinence garment having side-edge-leakage-guard gutters configured to contain free liquids within the garment. Each of these patents are incorporated herein by reference. While each elasticized leg cuff 32 may be configured so as to be similar to any of the leg bands, side flaps, barrier cuffs, or elastic cuffs described above, it is preferred that each elasticized leg cuff 32 comprise at least an inner barrier cuff 84 comprising a barrier flap and a spacing element such as described in the above-referenced U.S. Pat. No. 4,909,803. In a preferred embodiment, the elasticized leg cuff 32 additionally comprises an elastic gasketing cuff 104 with one or more elastic strands, positioned outboard of the barrier cuff 84 such as described in the above-referred U.S. Pat. No. 4,695,278.

The diaper 20 preferably further comprises an elasticized waistband 34 that helps provide improved fit and containment. The elasticized waistband 34 is that portion or zone of the diaper 20 which is intended to elastically expand and contract to dynamically fit the wearer's waist. The elasticized waistband 34 preferably extends longitudinally outwardly from at least one of the waist edges 57 of the absorbent core 28 and generally forms at least a portion of the end edge 52 of the diaper 20. Disposable diapers are generally constructed so as to have two elasticized waistbands, one positioned in the rear waist region 44 and one positioned in the front waist region 46, although diapers can be constructed with a single elasticized waistband. Further, while the elasticized waistband 34 or any of its constituent elements can comprise a separate element affixed to the diaper 20, the elasticized waistband 34 may be constructed as an extension of other elements of the diaper such as the backsheet 26 or the topsheet 24, preferably both the backsheet 26 and the topsheet 24. The elasticized waistband 34 may be constructed in a number of different configurations including those described in U.S. Pat. No. 4,515,595 entitled "Disposable Diapers with Elastically Contractible Waistbands" issued to Kievit et al. on May 7, 1985 and the above referenced U.S. Pat. No. 5,151,092 issued to Buell; each of these references being incorporated herein by reference.

The elasticized waistband 34 may comprise any suitable stretchable or elastomeric materials. (As used herein, the term "stretchable" refers to materials that are extensible when forces are applied to the material, and offer some resistance to extension. The term "elastomeric" refers to materials that extend in at least one direction when a force is applied to the material, and return to approximately their original dimensions after the force is released.) Suitable elastomeric materials for use as the elasticized waistband 34 are described hereinbelow with respect to the elasticized side panels 30.

In a preferred embodiment, the diaper 20 also comprises elasticized side panels 30 disposed in the rear waist region 44. (As used herein, the term "disposed" is used to mean that an element(s) of the diaper is formed (joined and positioned) in a particular place or position as a unitary structure with other elements of the diaper or as a separate element joined to another element of the diaper.) The elasticized side panels 30 provide an elastically extensible feature that provides a more comfortable and contouring fit by initially conformably fitting the diaper to the wearer and sustaining this fit throughout the time of wear well passed when the diaper has been loaded with exudates since the elasticized side panels allow the sides of the diaper to expand and contract. The elasticized side panels 30 further provide more effective application of the diaper 20 since even if the diaperer pulls one elasticized side panel 30 farther than the other during the application (asymmetrically), the diaper 20 will "self-adjust" during wear. While the diaper 20 of the present invention preferably has the elasticized side panels 30 disposed in the rear waist region 44; alternatively, the diaper 20 may also be provided with elasticized side panels disposed in the front waist region 46 and the rear waist region 44. While the elasticized side panels 30 may be constructed in a number of configurations, examples of diapers with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; and in U.S. Pat. No. 5,151,092 issued to Buell et al. on Sep. 29, 1992; each of which are incorporated herein by reference. Suitable elastic materials for use as the elasticized side panels include elastomeric foams, synthetic or natural rubber, synthetic or natural rubber foams, elastomeric films, elastomeric scrim, elastomeric woven or nonwoven webs, elastomeric composites such as elastomeric nonwoven laminates, or the like.

The diaper 20 also comprises a fastening system 36 which forms a side closure which maintains the rear waist region 44 and the front waist region 46 in an overlapping configuration such that lateral tensions are maintained around the circumference of the diaper to maintain the diaper on the wearer. As shown in FIG. 2, the fastening system 36 comprises a securement member 37 disposed adjacent each longitudinal edge 50 in the rear waist region 44, and at least one landing member 38 disposed in the front waist region 46 so as to form a portion of the outer surface 42. Each securement member 37 preferably comprises a tape tab 120 and a first fastening component 122. The landing member 38 preferably comprises a complimentary second fastening component 124 engageable with the first fastening component 122 of the securement member 37. An exemplary fastening system wherein the first and second fastening components each comprise mechanical closure elements comprising hook and loop fastening materials is disclosed in U.S. Pat. No. 4,869,724 issued to Scripps on Sep. 26, 1989. The fastening systems utilizing mechanical closure elements are also disclosed in U.S. Pat. No. 4,846,815 issued to Scripps on Jul. 11, 1989; and U.S. Pat. No. 4,894,060 issued to Nestegard on Jan. 16, 1990. A fastening system having combination adhesive/mechanical closure elements as described in U.S. Pat. No. 4,946,527 issued to Battrell on Aug. 7, 1990. Each of these patents are incorporated herein by reference. In a preferred embodiment of the present invention as is shown in FIG. 2, the fastening system 36 comprises an adhesive tape tab fastening system comprising a tape tab 120 having an adhesive attachment layer 126 and a landing member 38 comprising a reinforcing strip 128 joined to the backsheet 26. Examples of such adhesive tape tab fastening systems are disclosed in U.S. Pat. No. 3,848,594 issued to Buell on Nov. 19, 1974; and the adhesive tape tabs, reinforcing strip, and indicia means disclosed in U.S. Pat. No. 4,662,875 issued to Hirotsu and Robertson on May 5, 1987. Each of these patents are incorporated herein by reference.

Each securement member 37 of the fastening system 36 is intended to provide a fastening means for engaging the landing member 38 so as to provide a secure, preferably a variable positioning side closure for the diaper 20. Thus, the securement member 37 comprises at least one fastening component. Each securement member 37 also preferably comprises a means for positioning the fastening component adjacent the landing member 38 so as to achieve an optimum fitting side closure. Thus, the securement member 37 may comprise any of the well known configurations and means for achieving a side closure on a diaper such as a patch or strip of a fastening component disposed to form a portion of the inner surface of the diaper or a tape tab having a fastening component positioned thereon.

Figure 4:
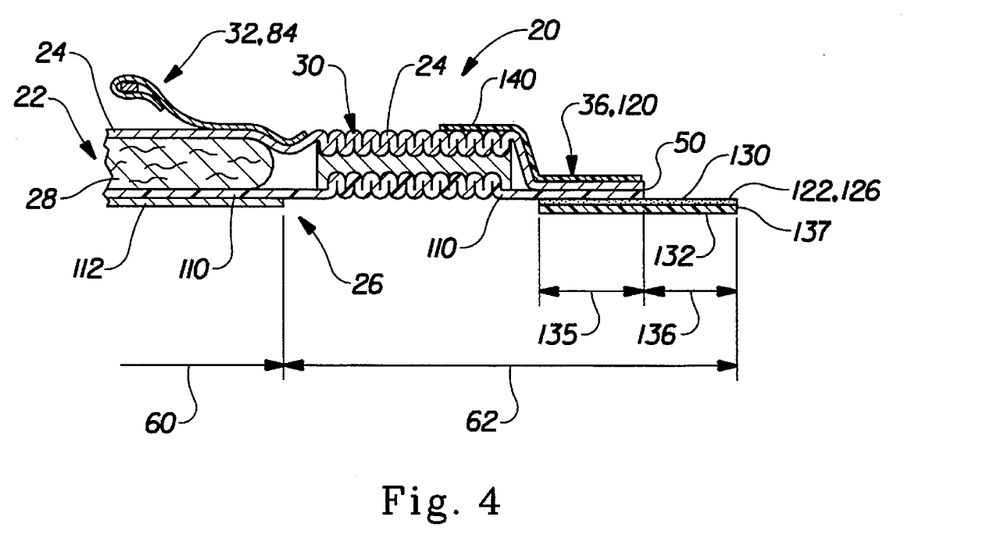
FIG. 4 is an inverted fragmentary sectional view of the disposable diaper shown in FIG. 2 taken along section line 4—4 of FIG. 2.

As shown in FIG. 2, each securement member 37 preferably comprises a tape tab 120. Any of the well known configurations and constructions of a tape tab may be used in the present invention. For example, an exemplary tape tab is described in detail in U.S. Pat. No. 3,848,594 issued to Buell on Nov. 19, 1974, and which patent is incorporated herein by reference. A particularly preferred tape tab 120 is illustrated in FIG. 4, and has a fastening surface 130 and a backing surface 132. The fastening surface 130 is that surface of the tape tab 120 designed to engage the landing member 38 of the present invention. Thus, the fastening surface 130 of the tape tab 120 is generally oriented to face the inner surface of the diaper 20. The backing surface 132 is that surface opposed to the fastening surface 130 and generally faces the outer surface of the diaper 20. The backing surface 130 is thus generally exposed during wear of the diaper 20. The preferred tape tab 120 illustrated in FIG. 4 is one in which is joined to the inner layer 110 of backsheet 26 to create a fixed portion 135 (i.e., that end of the tape tab 120 joined to the diaper 20 during manufacture). The tape tab 120 has another element which is the tab portion 136 (i.e., that end of the tape tab 120 that extends outwardly beyond the longitudinal edge 50 of the diaper 20 and that is grasped by the diaperer in securing the diaper on the wearer). The distal edge 137 of the tape tab 120 preferably has rounded corners to eliminate the possibility of harsh corner edges contacting the wearer's skin so as to prevent stomach redmarking. The preferred tape tab 120 of the present invention also comprises a release portion 140 joined to the topsheet 24 of the diaper 20. The release portion 140 allows the tab portion 136 to be inwardly folded during manufacture to protect the adhesive attachment layer 126 from contamination or delamination prior to use. As shown in FIG. 4, the release portion 140 extends inwardly from the longitudinal edge 50 of the diaper 20 preferably up to and juxtaposed over a portion of the elasticized side panel 30. The tab portion 136 is also preferably shorter in the lateral direction (width) than the release portion 140 so that it is easier for the diaperer to initially grasp the tab portion 136.

As shown in FIG. 4, the fixed portion 135 is joined to the inner layer 110 which is comprised of liquid impervious plastic material. The fixed portion 135 preferably resides within the side region 62 and does not extend into the central region 60. Thus, the fixed portion 135 is joined directly to the inner layer 110. The fixed portion 135 does not extend over and is not joined to any portion of the nonwoven fibrous outer layer 112. By having the fixed portion 135 of tape tab 120 joined only to the inner layer of liquid impervious plastic material 110, the tape tab 120 is less likely to separate from the diaper 20 during application and/or wear than if the fixed portion 135 was joined to a nonwoven fibrous layer which would provide a weaker bond possibly allowing the tape tab to separate from the diaper 20 during application and/or wear of the diaper.

The fastening component of the securement member 37 forms a closure between the securement member and the complimentary fastening component of the landing member 38. Thus, the fastening component provides a means for engaging the complimentary fastening component of the landing member 38 to maintain the front waist region 46 and the rear waist region 44 in an overlapping configuration to provide a secure side closure for the diaper 20. Further, it is preferred that a diaper fit a range of different size wearers and that the fastening system be simple and easy to use. Therefore, the fastening components should allow for variable positioning of the zone of closure so that the diaper may fit a range of sizes while also being simple to fasten with minimal effort. The fastening components thus comprise any of the well known attachment means for achieving an adjustable positioning secure closure as defined hereinafter. Examples of such adjustable positioning attachment means include an adhesive attachment layer such as a pressure-sensitive adhesive as are known in the art, a mechanical closure element such as a hook fastening material or a loop fastening material, any cohesive materials as are known in the art, or a combination of an adhesive/mechanical closure element.

The first fastening component 122 is preferably a separate material, such as an adhesive attachment layer or a mechanical closure element, positioned on and joined to the tape tab 120. As shown in FIG. 4, the first fastening component 122 preferably comprises an adhesive attachment layer 126 coated on the tab portion 136 to form the fastening surface 130.

The first fastening component 122 may be positioned anywhere on the securement member 37. When the securement member 37 comprises a tape tab 120, the first fastening component 122 is preferably positioned either on all or at least a portion of the fastening surface 130 of the tab portion 136. The first fastening component 122 may comprise a combination adhesive/mechanical closure element having an adhesive attachment layer and a mechanical closure element disposed on another area of the tab portion 136 on the fastening surface 130 and adjacent the distal edge 137 of the tape tab 120. An exemplary embodiment of this configuration is disclosed in U.S. Pat. No. 4,869,724 issued to Scripps on Sep. 26, 1989, which is incorporated herein by reference.

The landing member 38 of the fastening system 36 provides a means for securing itself to the securement member 37 to provide a side closure and to maintain the front waist region 46 and the rear waist region 44 in an overlapping configuration. The landing member 38 may be disposed anywhere on the diaper 20 so long as it can engage the securement member 37 so as to provide the side closure, and preferably a variable positioning side closure. Because the landing member 38 determines the approximate location of where the securement member 37 should be placed for optimum fit, the landing member 38 is preferably positioned so as to achieve variable positioning of the side closure to that the diaper may fit a range of sizes, so that an overlap between the front waist region 46 and the rear waist region 44 is achieved. The landing member 38 is preferably centered about the longitudinal centerline 100 in the front waist region 46 and extends laterally outwardly.

The landing member 38 may either be a discreet, separate element or elements joined to the diaper 20 or a unitary piece of material with an element of the diaper 20. The landing member 38 may thus comprise, for example, the topsheet 24 or the backsheet 26. While the landing member 38 can assume varying sizes and shapes, it preferably comprises one or more patches of material joined to the backsheet 26 in the front waist region 46 that allows for maximum fit adjustment of diaper 20 to the wearer. In a preferred embodiment of the diaper 20, as illustrated in FIG. 2, the landing member 38 has an elongate, rectangular shape and is secured to the backsheet 26 in the front waist region 46 by an adhesive attachment means (not shown). The landing member 38 comprises a fastening component (second fastening component 124) engageable with the fastening component of the securement member 37 (first fastening component 122). Thus, the fastening component of the landing member 38 (second fastening component 124) may be manufactured from a wide range of materials and configurations capable of securely engaging the fastening component of the securement member 37 (first fastening component 122).

When the first fastening component 122 of securement member 37 comprises an adhesive attachment layer 126, the second fastening component 124 of the landing member 38 preferably comprises a reinforcing strip 128. When the first fastening component 122 of the securement member 37 comprises a mechanical closure element, a second fastening component 124 also comprises a mechanical closure element. Thus, when the first fastening component 122 comprises a hook fastening material, the second fastening component 124 preferably comprises a loop fastening material.

In a preferred embodiment of the present invention, the landing member 38 preferably comprises a reinforcing strip 128 releasably engageable with the adhesive attachment layer 126 of the tape tabs 120. The reinforcing strip 128 may comprise any number of configurations and materials secured to the backsheet 26 of the diaper 20. The reinforcing strip 128 is preferably a separate member secured to the backsheet 26 to form a portion of the outer surface 42 of the diaper 20. A preferred reinforcing strip 128 comprises a sheet of biaxially oriented polypropylene film.

The reinforcing strip 128 is also preferably provided with indicia means 150 for aiding the diaperer in fitting the diaper to a wearer to obtain optimal waist fit and leg opening fit. The indicia means 150 may be any type of lines, patterns, ornamental designs, symbols, script, color codes, or other markings which have the capability, either inherently or with additional denotation, to aid an individual fitting the diaper to the wearer to promptly locate the desired affixation points for a particular tape tab fastener. Such indicia means 150 are more fully described in U.S. Pat. No. 4,662,875 issued to Hirotsu and Robertson on May 5, 1987, and which is incorporated herein by reference.

The diaper 20 may also comprise a disposal means that allows convenient and easy disposal of the diaper 20. Thus, the disposal means may be any structure that allows the diaper 20 to be folded or rolled up into a configuration for disposal and secured in that configuration to contain the contents within the soiled diaper. An example of such a disposal means is disclosed in U.S. Pat. No. 4,963,140 issued to Robertson et al. on Oct. 16, 1990, and which patent is incorporated herein by reference.

In use, the diaper 20 is preferably applied to the wearer by positioning the rear waist region 44 under the wearer's back and drawing the remainder of the diaper 20 between the legs of the wearer so that the front waist region 46 is positioned across the front of the wearer. The tape tabs of the fastening system are then released from the release portion. The diaperer then wraps the elasticized side panel around the wearer, while still grasping the tab portion. The fastening system is secured to the outer surface of the diaper to effect a side closure.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article having a rear waist region, a front waist region, a crotch region, a central region, a pair of side regions, a pair of longitudinal edges, and a pair of end edges, said absorbent article comprising:

a liquid pervious topsheet;

a backsheet joined to said topsheet, said backsheet comprising an inner layer of liquid impervious plastic material and an outer layer of nonwoven fibrous material, said outer layer being positioned between said side regions such as not to form any portion of the longitudinal edges and extending from said rear waist region to said front waist region;

an absorbent core positioned between said topsheet and said backsheet; and a fastening system comprising a pair of securement members and a landing member, said securement members comprising a tape tab having a fixed portion and a tab portion, said fixed portion being joined to said inner layer of liquid impervious plastic material and not to said outer layer of nonwoven fibrous material.

2. The absorbent article of claim 1 wherein said outer layer forms a portion of at least one of said end edges.

3. The absorbent article of claim 2 wherein said outer layer forms a portion of each of said end edges.

4. The absorbent article of claim 1 wherein said pair of securement members comprises a hook fastening material.

5. The absorbent article of claim 1 wherein said landing member comprises a loop fastening material.

6. A disposable absorbent article having a rear waist region, a front waist region, a crotch region, a central region, a pair of side regions, a pair of longitudinal edges, and a pair of end edges, said absorbent article comprising:

a liquid pervious topsheet;

a backsheet joined to said topsheet, said backsheet comprising an inner layer of liquid impervious plastic material and an outer layer of nonwoven fibrous material, said outer layer being positioned within said central region such as not to form any portion of the longitudinal edges or the end edges;

an absorbent core positioned between said topsheet and said backsheet; and a fastening system comprising a pair of securement members and a landing member, said securement members comprising a tape tab having a fixed portion and a tab portion, said fixed portion being joined to said inner layer of liquid impervious plastic material and not to said outer layer of nonwoven fibrous material.

\* \* \* \* \*